United States Patent [19]
Gangemi et al.

[11] Patent Number: 5,558,639
[45] Date of Patent: Sep. 24, 1996

[54] AMBULATORY PATIENT INFUSION APPARATUS

[76] Inventors: Ronald J. Gangemi, 10607 Banner Mine Way; David Stokes, 11076 Sky Pines Ridge, both of Nevada City, Calif. 95959

[21] Appl. No.: 75,144

[22] Filed: Jun. 10, 1993

[51] Int. Cl.$^6$ .................................................. A61M 31/00
[52] U.S. Cl. ........................... 604/67; 604/152; 417/360; 222/63; 222/325
[58] Field of Search ............ 604/152, 67; 128/DIG. 12, 128/DIG. 13; 417/42, 43, 63, 360, 477.2; 222/52, 63, 309, 325, 333, 383.1

[56] References Cited

U.S. PATENT DOCUMENTS

| | | | |
|---|---|---|---|
| 4,346,705 | 8/1982 | Pekkarinen et al. | 604/152 |
| 4,396,385 | 8/1983 | Kelly et al. | 604/152 |
| 4,447,234 | 5/1984 | Mayfield | 604/152 |
| 4,474,309 | 10/1984 | Solomon | 604/152 |
| 4,519,792 | 5/1985 | Dawe | 604/152 |
| 4,559,038 | 12/1985 | Berg et al. | |
| 4,565,542 | 1/1986 | Berg | |
| 4,605,396 | 8/1986 | Tseo et al. | 604/152 |
| 4,650,469 | 3/1987 | Berg et al. | |
| 4,747,828 | 5/1988 | Tseo | 604/67 |
| 4,850,805 | 7/1989 | Madsen et al. | 604/152 |
| 5,292,306 | 3/1994 | Wynkoup et al. | 604/152 |

*Primary Examiner*—Randall L. Green
*Assistant Examiner*—Mark Bockelman
*Attorney, Agent, or Firm*—John G. Mesaros

[57] ABSTRACT

A modular ambulatory patient infusion apparatus including a control module and an infusion fluid or solution-containing interlocking cassette. The control module includes thumbwheel presettable electronic circuitry and display means in the form of windows for viewing the preset numerical values. In accordance with these settings, the circuitry drives a motor-operated reciprocable piston actuator terminating in a finger-like flange engaging portion. The motor shaft drives a worm and worm gear arrangement for reciprocating the piston actuator, with each of the worm and worm gear interoperatively associated with light cells for determining both motor speed and worm gear revolution. These, in turn, provide signals to the circuitry to vary the duty cycle of a pulse width modulated motor controller, while providing an indication of a complete revolution of the worm gear (which correlates to one cycle of the piston actuator) and providing an indication of motor speed which is utilized to detect occlusions by motor speed slowdown or stall. A flexible solution bag is retained within the cassette with the discharge tube thereof in fluid communication with a fluid pumping means within a block having a chamber therein and valve arrangement therein. The fluid pump includes a piston communicating with the chamber and having a flanged end configured for coacting engagement with the finger-like flange engaging portion of the piston actuator of the control module. The valve arrangement includes first and second check valves in fluid flow communication with the chamber, the first valve being in flow communication with the tube from the bag and the second valve being in flow communication with a passage leading to an IV tube set for connection to the patient.

33 Claims, 5 Drawing Sheets

AMBULATORY PATIENT INFUSION APPARATUS

BACKGROUND OF THE INVENTION

The background of the invention will be discussed in two parts.

1. Field of the Invention

This invention relates to infusion apparatus and more particularly to portable infusion apparatus which may be carried on the person of an ambulatory patient without connection to an external power source.

2. Description of the Prior Art

Infusion apparatus for ambulatory patients requires that the apparatus be of lightweight for carrying by the patient. Preferably such devices include some battery operated mechanism for actuation of means for discharging fluid at a controlled rate to a maximum amount over a treatment period to a patient, usually by intravenous means.

One such apparatus is shown and described in U.S. Pat. Nos. 4,650,469 and 4,559,038, issued on Mar. 17, 1987 and Dec. 17, 1985, respectively, to Berg et at., both such patent being entitled "Drug Delivery System". A third companion case, U.S. Pat. No. 4,565,542 issued to Berg on Jan. 21, 1986, and is entitled "Locking Mechanism for a Drug Delivery System". The device in those patents is modularly constructed and relates to a drug delivery system for ambulatory patient use and includes a control module and an interlocking reservoir module. The reservoir module contains a drug container bag therein with the tube thereof supported longitudinally on a pressure plate. With the reservoir module connected to the control module, a motor controlled camshaft of a pumping mechanism reciprocates a plurality of valves and an expulsor in the control module for engaging and interacting with the tube located on the pressure plate for forcing the drug from the container bag to the patient.

Such a device requires a complex pumping and valving mechanism which complexity adds to both weight and cost. Furthermore, since the reciprocating valves act against the external surface of the elastomeric tube, any variations in tube elasticity and wall thickness could conceivably affect the discharge rate and accuracy of the drug delivery system.

In accordance with an aspect of the present invention, there is provided a new and improved modular infusion apparatus with a new and improved fluid delivery system of economical construction which operates on the fluid rather than the delivery tube.

In accordance with another aspect of the invention, the controls for setting the variables needed for the dispensing of solution are positioned in such a way as to be concealed and inaccessible during use by the patient.

Another feature of the invention relates to the interlocking arrangement between the cassette and the control module.

SUMMARY OF THE INVENTION

The foregoing aspects and other objects and features of the invention are accomplished by providing a modular ambulatory patient infusion apparatus including a control module and an infusion fluid or solution-containing interlocking cassette. The control module includes thumbwheel presettable electronic circuitry and display means in the form of windows for viewing the preset numerical values. In accordance with these settings, the circuitry drives a motor-operated reciprocable piston actuator terminating in a finger-like flange engaging portion. The motor shaft drives a worm and worm gear arrangement for reciprocating the piston actuator, with each of the worm and worm gear interoperatively associated with light cells for determining both motor speed (from the worm) and worm gear revolution (from the worm gear light cell). These, in turn, provide signals to the circuitry to vary the duty cycle of a pulse width modulated motor controller, while providing an indication of a complete revolution of the worm gear (which correlates to one cycle of the piston actuator) and providing an indication of motor speed which is utilized to detect occlusions by motor speed slowdown or stall.

The cassette housing includes a spring catch and longitudinally arranged, outwardly extending interrupted flange portions which matingly coact with longitudinally arranged inwardly extending flange portions on the control module for enabling sliding interlock of the two parts. A fluid receiving flexible bag is retained within the cassette with the discharge tube thereof in fluid communication with a fluid pumping means within a block having a chamber therein and including a valve arrangement therein. The fluid pumping block includes a piston communicating with the chamber and having a flanged end configured for coacting engagement with the finger-like flange engaging portion of the piston actuator of the control module. The valve arrangement includes first and second check valves in fluid flow communication with the chamber, the first valve being in flow communication with the tube from the bag and the second valve being in flow communication with a passage leading to an IV tube set for connection to the patient. The first valve is actuable to an open condition on withdraw of the piston and draws fluid easily from the bag to the chamber with virtually no pressure. The second valve is normally closed during the drawing motion of the piston and requires a higher pressure to open, the opening thereof occurring on movement of the piston inwardly toward the chamber to pump fluid from the chamber into the patient discharge tubing set. In the event of occlusion of the discharge tubing set, the motor speed will slow down or stall, in which event the control module sounds an alarm and disconnects the motor circuit.

Other objects, features and advantages of the invention will become apparent from a reading of the specification when taken in conjunction with the drawings in which like reference numerals refer to like elements in the several views.

DESCRIPTION OF THE PREFERRED EMBODIMENT

Figure 1:
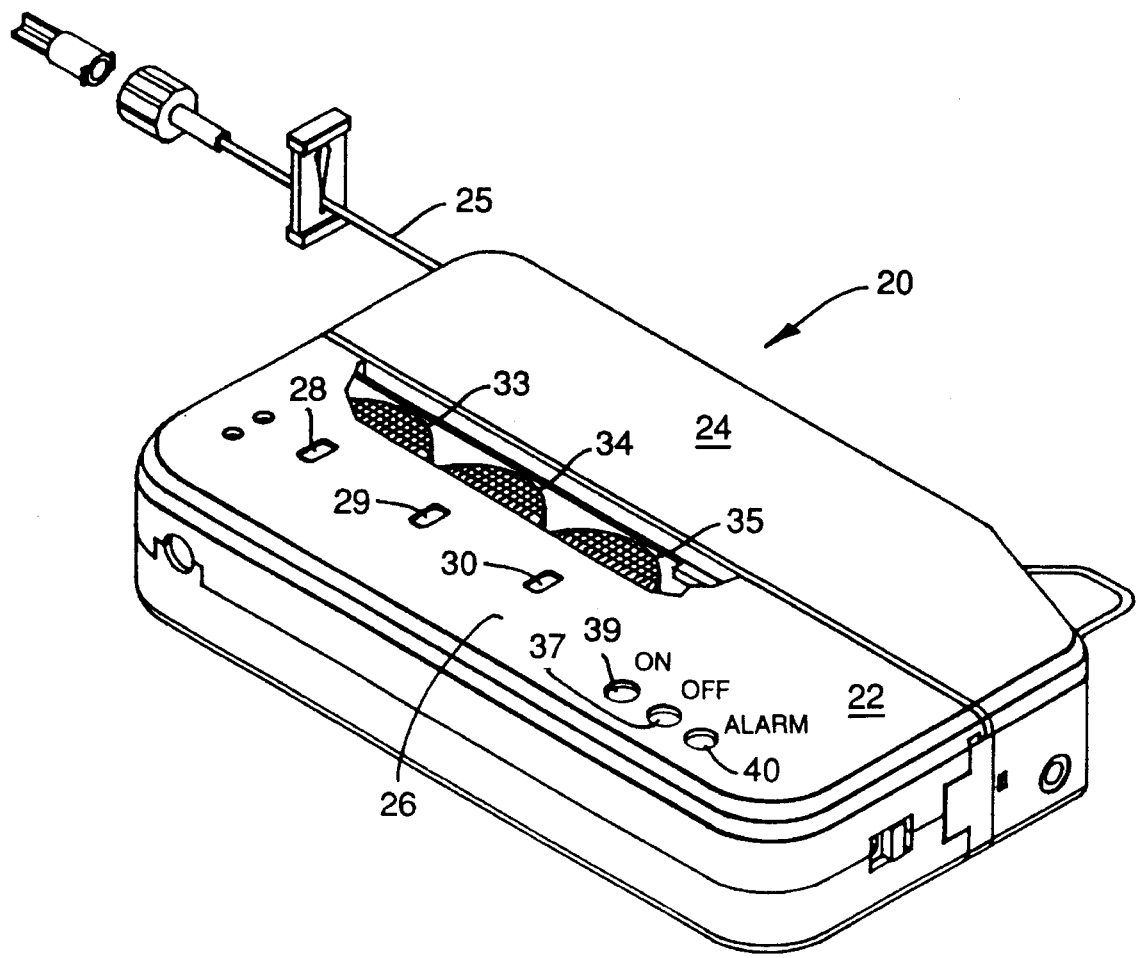
FIG. 1 is a perspective view, partially broken away, of the ambulatory patient modular infusion apparatus according to the invention.

Referring now to the drawings, and particularly to FIG. 1, there is shown an infusion apparatus, generally designated 20, which is shown in its assembled or ready-for-use condition, and includes a control module, generally designated 22 and a fluid chamber or solution bag containing cassette, generally designated 24, having a solution discharge tube 25 protruding from the side thereof. The apparatus 20 is generally box-like in configuration, with dimensions of about six inches by three and one-half inches by about one inch. The cassette 24 may be provided in various sizes, such as a 100 ml cassette or a 250 ml cassette, with the weight for the apparatus 20 containing the latter volume of solution weighing about twenty ounces. The face portion or surface 26 of the control module 22 includes display means which may be of any convenient construction. In the preferred embodiment, the display means are in the form of first, second and third display windows 28–30 which, respectively, display fluid flow rate, the desired fluid volume, and the cycle, that is, dosage frequency during a given period. The windows 28–30 are apertures formed in the housing of the control module, beneath which lie first, second and third thumbwheels 33–35 (the edges of which are viewable through the broken away portion showing the side or interconnecting surface of the module 22), each of which includes indicia about the periphery of the surface thereof facing the windows 28–30. The thumbwheel switches 33–35 may be, for example, 16 position rotary switches. The variables displayed may include, for example, flow rate specified ml/hour; volume in ml, and frequency in the number of cycles per day. The surface 26 also has provision for an alarm indicator 37, an "on" indicator 39 and an "off" indicator 40, each of which may be a light emitting diode, with the on and off indicators being positioned adjacent a membrane switch therebelow.

Figure 2:
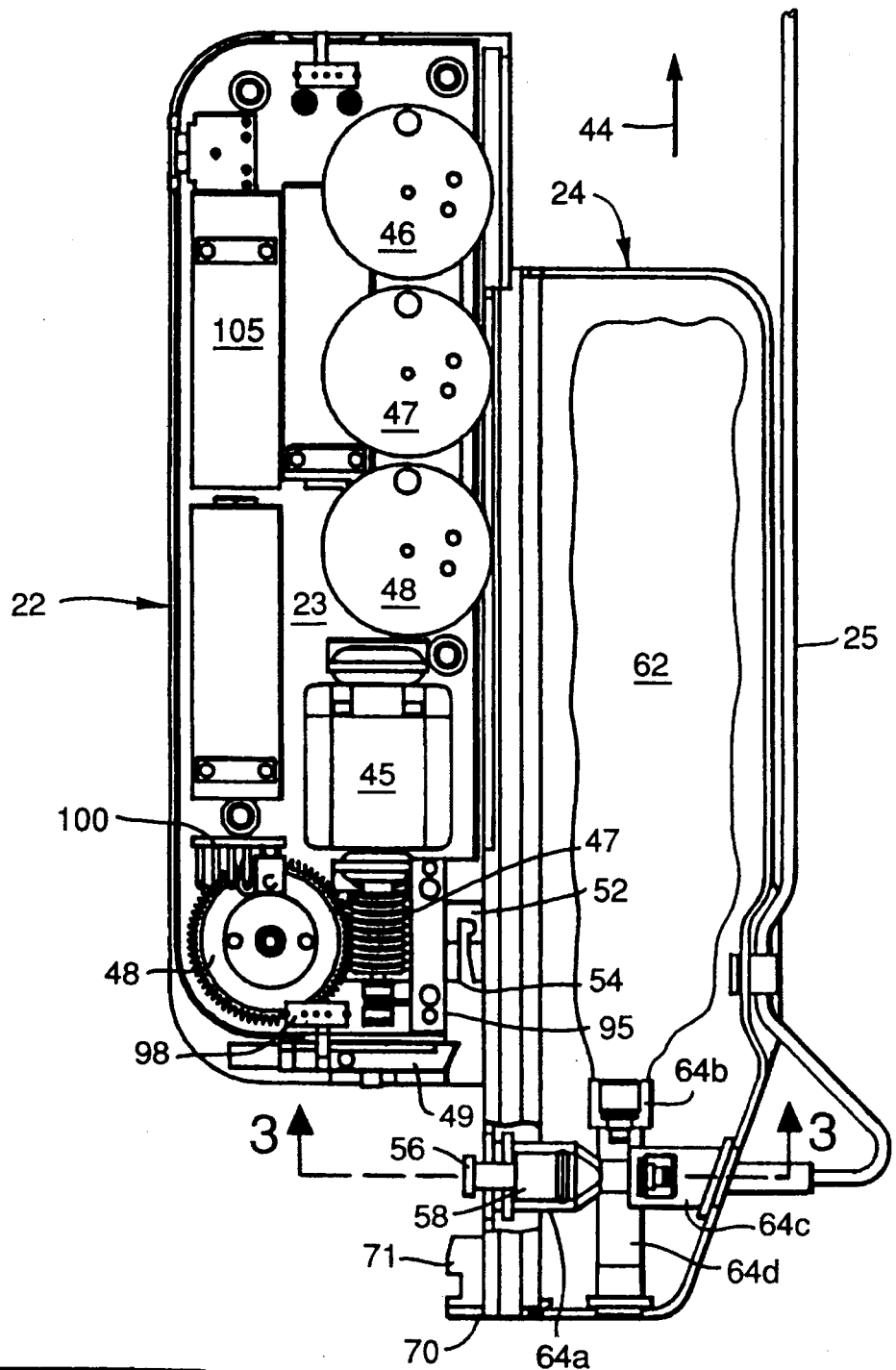
FIG. 2 is a plan view, partially broken away, of the infusion apparatus of FIG. 1 showing the control module and the cassette in partially connected relationship.

FIG. 2 depicts the module 22 and the cassette 24 in partially connected relationship. The interconnecting flange portions of the cassette 24 and control module 22 are matingly configured for coacting engagement ion positioning the two parts in abutting offset relationship and then sliding of the cassette 24 in the direction of the arrow 44. positions. The control module 22 includes a box-like housing having upper and lower housing portions configured to form an enclosure for receiving therein a plurality of suitable control means, such as the rotatable thumbwheels 33–35, which lie in a common plane with the edges thereof protruding through slots (See also FIG. 1) formed in the cassette-engaging surface of the control module 22 housing. On interconnection of the parts as shown in FIG. 1, the thumbwheels 33–35 are inaccessible to the user of the apparatus 20. The lower housing portion 25 of the control module also receives therein a motor drive assembly including a battery operated motor 45, the shaft 46 of which carries a worm 47 engaging a gear 48, the axis of rotation of which lies in a plane perpendicular to the plane of the lower surface of the housing portion 23 adjacent the lower end thereof (as viewed in FIG. 2). The gear 48 drives a cam 50 which reciprocates a piston actuator 52, the terminal end of which is formed as a hook 54, the dimensions and configuration thereof being sufficient for enabling releasable frictional coupling to a mushroom-shaped or ranged head 56 of a piston 58 operating within a cylinder or bore of a fluid control valve assembly, generally designated 60, within the lower end of the housing of the cassette 24.

Figure 3:
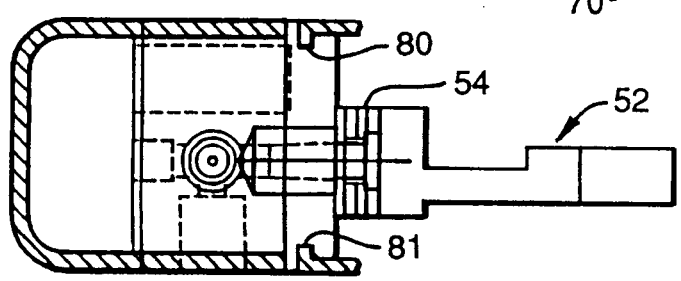
FIG. 3 is a cross-sectional view of the cassette taken along line 3—3 of FIG. 2.
Figure 4:
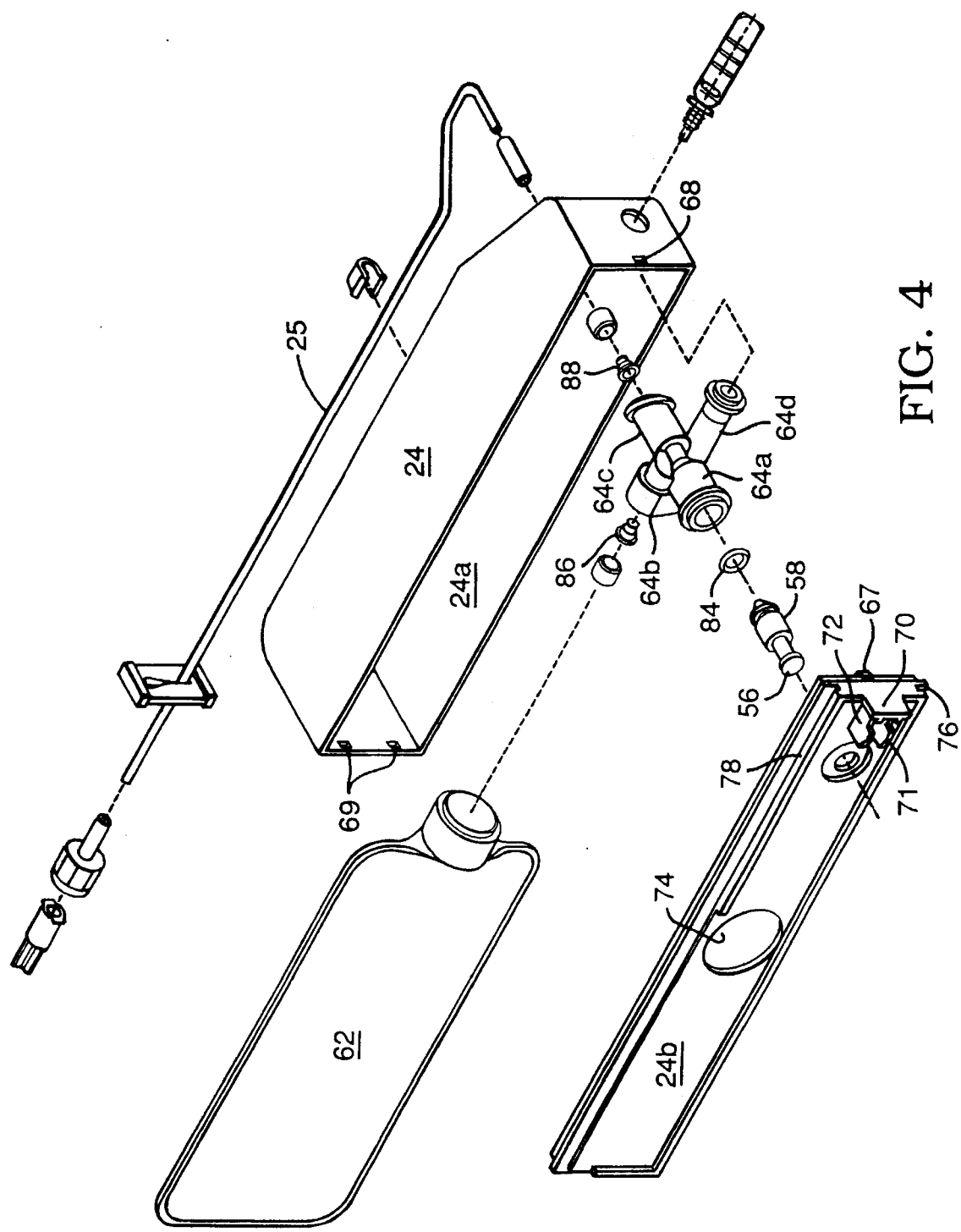
FIG. 4 is an exploded perspective view of the cassette of the infusion apparatus of FIG. 1.

As shown in FIGS. 1 through 4, the cassette 22 is a hollow box-like housing forming an enclosure for receiving therein a flexible pouch or fluid bag 62 and a fluid or solution control valve assembly, generally designated 64. As best shown in FIG. 4, the assembly 64 includes a valve block having a bore section 64a configured for receiving the actuator piston 58 therein, an inlet bore section 64b configured for interconnection to the bag 62 via an inlet valve assembly, a discharge bore section 64c configured for connection to the tubing set 25 and a fill port section 64d which is accessible for filling the bag 62 from the exterior of the cassette 24. The housing of the cassette 24 includes an elongate trough shaped portion 24a and an elongate closing/coupling plate 24b which is configured with tang members at the lower and upper longitudinally opposite edges, only one tang 67 being shown. The tangs 67 detentingly engage matingly configured slots 68 and 69 in the corresponding positions of the facing open end of the housing portion 24a and, upon detenting engagement close the open end of the trough-shaped housing portion 24a.

The lower end of the plate 24b is provided with a transversely extending tab 70 having a pair of generally parallel spaced hook members 71, 72 extending upwardly therefrom with the hook portions directed toward engagement with mating means in the lower end of the control module 22 housing, the mating means being formed by a rib 49 (See FIG. 2). The plate 24b is also provided with a centrally positioned enlarged aperture 74 which provides venting during filling of solution or discharging of solution from the bag 62. Opposite long edges of the plate 24b are provided with slots 76, 78. Slot 78 extending only part of the length of the plate 24b. The corresponding engaging edges of the control module housing are provided with inwardly extending aligned ribs 80, 81 (See FIG. 3) for matingly slidingly engaging the slots 76, 78, with one of the ribs extending only a part of the length thereof for cooperative engagement with the slots as previously described in connection with the interlock operation in FIG. 2.

Referring now to FIGS. 2, 3 and 4, the valve assembly 64 has the bore 64a configured for slidably receiving therein the piston 58 which is provided with suitable sealing means, such as an O-ring 84, the piston 58 being actuated reciprocably by the motor 35 through rotation of the worm 47 and gear 48 which reciprocates the piston actuator 52 which is coupled to the flanged head 56 of piston 58 as shown in FIG. 3. First and second valve means, specifically inlet check valve member 86 and discharge check valve member 88 are fitted within the bores of sections 64b and 64c, respectively. Each of the valve members 86 and 88 is formed in one piece of elastic material which is nipple-shaped, each having a different durometer. The inlet check valve 86, at the smaller diameter or outer end, has a deep single slit with low durometer material to provide minimal resistance. The outlet or discharge valve member 88, at the smaller diameter or outer end, has a shallow slit and is formed of a higher durometer material to eliminate possible seepage up to approximately 36 inches of mercury. With the selected valve members 86 and 88, the outlet valve member 88, having the higher durometer rating, precludes any possibility of backflow, that is, in some instances arterial pressure of the patient is sufficiently high to force fluid back through the tubing set 25. In such instances, the outlet valve 88, having a high durometer and a shallow slit, precludes such backflow up to a pressure of at least one atmosphere.

Specifically, during operation, the valve arrangement includes these first and second check valves in fluid flow communication with the piston 58 bore or chamber, the first valve 86 being in flow communication with the solution the bag 62, and the second valve 88 being in flow communication with a passage leading to an IV tubing set 25 for connection to the patient. The first valve 86 is actuable to an open condition on withdraw of the piston 58 and is configured and constructed to permit fluid to be drawn easily from the bag 62 to the chamber with virtually no pressure. The second valve 88 is normally closed during the drawing motion of the piston 58 and has the durometer of the material thereof such that it requires a higher pressure to open, for example, about 2 psi, the opening thereof occurring on movement of the piston 58 inwardly toward the chamber to pump solution from the chamber into the patient discharge tubing set 25. In the event of occlusion of the discharge tubing set, the motor 45 speed will slow down or stall, in which event the control module sounds an alarm and disconnects the motor circuit. Infusion apparatus includes an IV tubing set, such as tubing set 25. On utilization of the apparatus, it is essential that some means be provided for "priming" the tubing, that is, some means must be provided for forcing solution from the solution bag, such as bag 62, through the tubing set 25. This "priming" is done in some suitable way so that solution is carried from the bag through the tubing until it exits therefrom, and this is done prior to attaching the IV set to the patient. In effect this "priming" discharges trapped air from the tubing set. In accordance with the instant invention, the piston 58 is configured so that the flanged head 56 thereof protrudes beyond the side of the cassette 22 where it is manually accessible, as a consequence of which it can be grasped by hand and reciprocated to manually prime the cassette 22 without the use of the power source, that is, force solution through the tubing set 25. In prior art devices such as those heretofore described, priming is accomplished after the parts of the apparatus are interconnected, thus using valuable battery energy to effect the priming.

Figure 6:
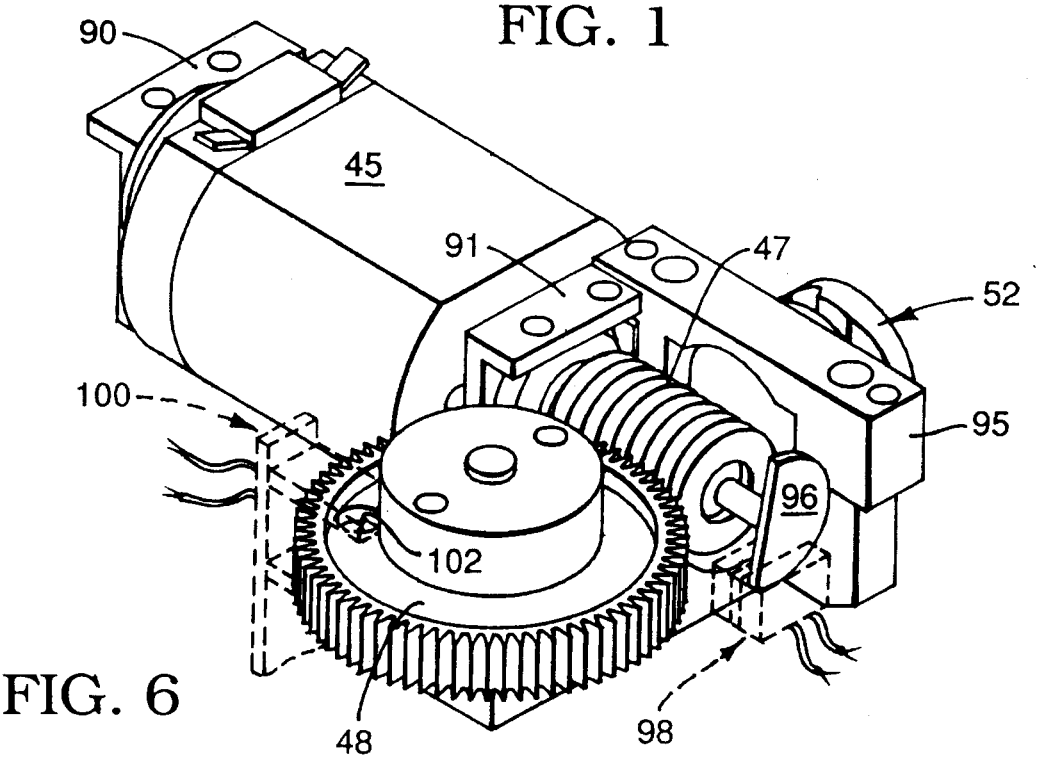
FIG. 6 is a perspective view of the motor drive of the control module of FIGS. 1 and 5.
Figure 5:
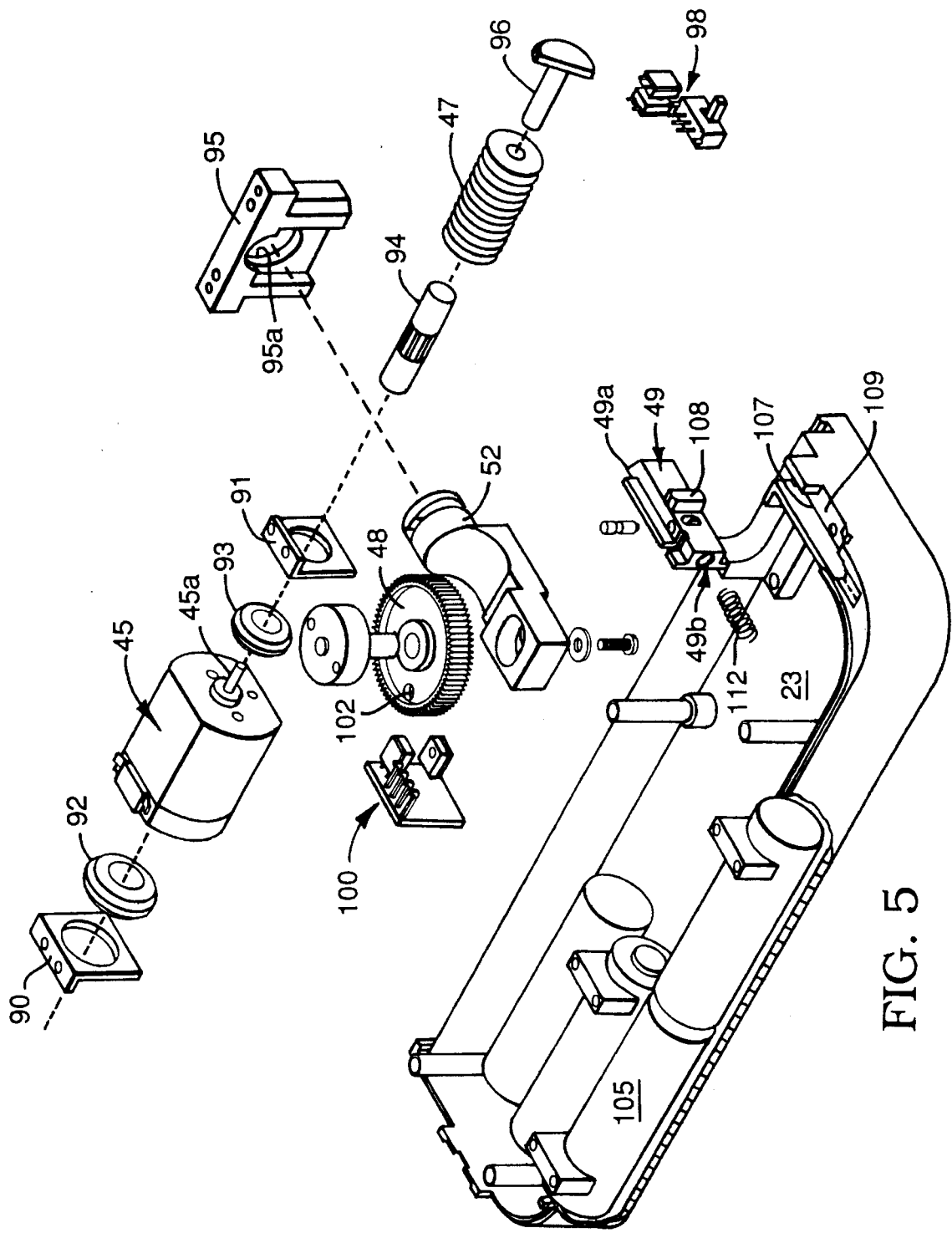
FIG. 5 is an exploded perspective view of the motor and drive elements of the control module of the apparatus of FIG. 1 in the lower housing portion with the upper cover removed.

Referring now to FIGS. 2, 5 and 6, the details pertaining to the construction of the control module 22 will be described. Referring first to FIG. 6, the motor assembly is shown and includes the motor 45 mounted between mounting blocks 90 and 91 with suitable bushing members 92, 93. The piston actuator 52 is supported by a support block 95 having an aperture 95a therein (See FIG. 5) for slidably receiving and supporting the body of actuator 58. The motor shaft 45a is coupled to a worm coupler shaft 94 which fits within the bore of the worm 47, the coupler 94 at its opposite end being connected to the shaft of a light interrupter segmented disc member 96. The member 96 is in the form of a disc with a portion thereof cut away. A first photo sensor assembly 98 has the disc member 96 received between the arms thereof with the light source and photocell thereof along a line which is interrupted on each rotation of the member 86. A second photo sensor assembly 100 is provided for cooperation with the gear 48 which has an aperture 102 formed therein on a line parallel to the axis of rotation thereof. The assembly 100 is positioned so that the light thereof passes through the aperture 102 when aligned with the light path, this photo sensor assembly 100 then being utilized to count rotations of the gear 48, and also to position a complete rotation of the gear 48 so that the light is passing through the aperture, this position corresponding to "top dead center" position of the piston actuator 52. Stated otherwise, by reference to FIG. 2, the actuator 52 will be at the position shown, this position being the extreme limit of travel of the actuator 52 to the left as viewed in FIG. 2.

As shown in FIG. 5, a battery pack 105 is fitted within the lower housing portion 23 of control module 24, the housing also having provision for receiving therein a printed circuit board (not shown) with the control logic thereon, as well as the thumbwheels 33–35. The lower edge of the housing portion 23 includes a groove 107 configured for slidably receiving therein a catch member, generally designated 49, the member 49 having a handle portion 108 protruding through a slot 109 for access thereto from the exterior of the apparatus 20. The catch member 49 has a tapered from end 49a which coacts with the hooks 71, 72 of the cassette 24, and a rear bore 49b which receives a spring member 112 to urge the catch member 49 into engagement with the hooks 71, 72.

Figure 7:
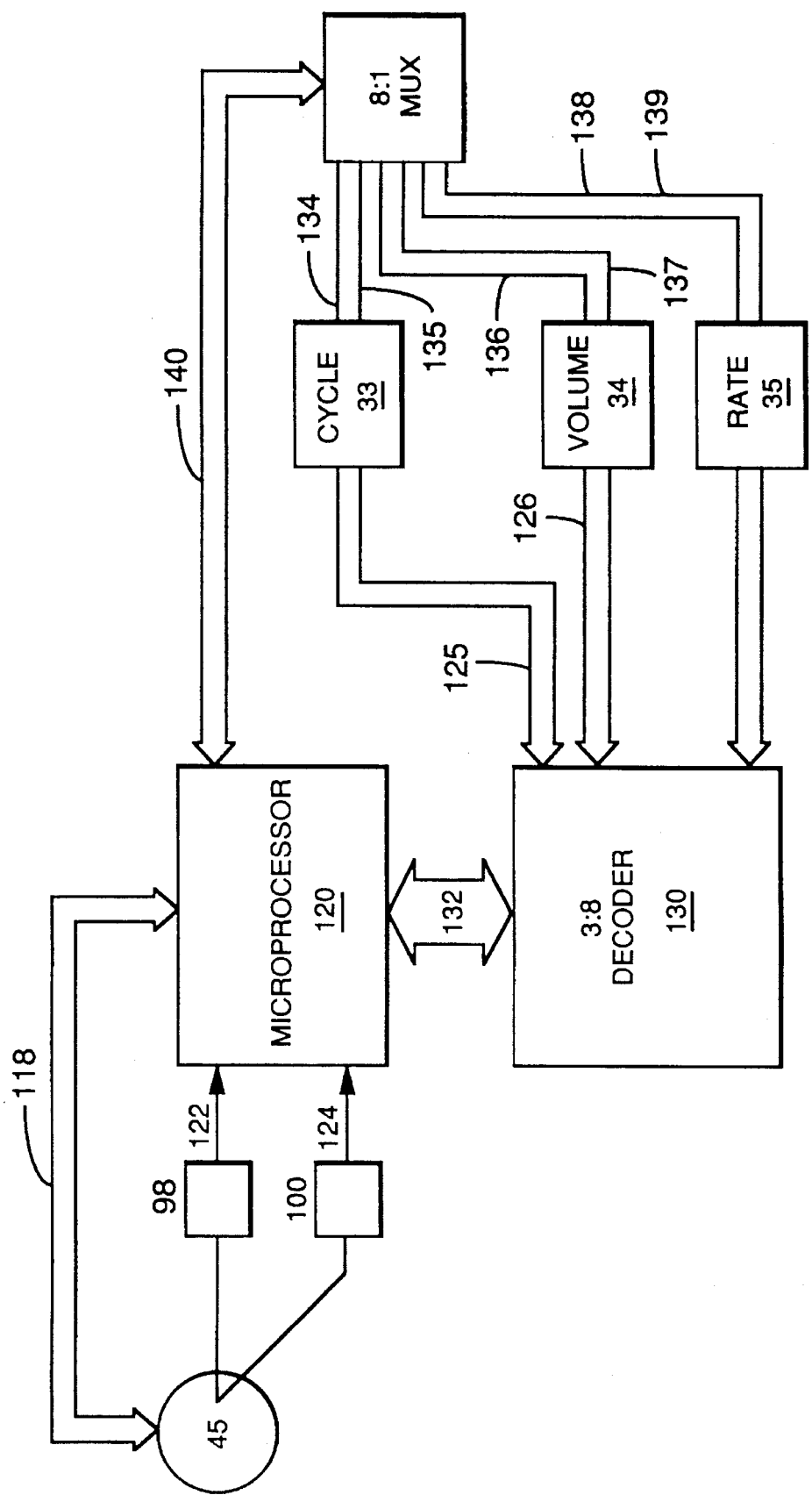
FIG. 7 is a block diagram of the electrical control elements of the apparatus of FIG. 1.

Referring now to FIG. 7, there is shown a block diagram of the electrical circuit of the apparatus 20. The motor 45 is controlled via line 118 by a microprocessor 120, which receives as inputs, the signals over lines 122 and 124 from the photo sensor assemblies 98 and 100. The microprocessor 120 is, for example a Xicor microprocessor model number 68HC705J2. Additional signals are received from the thumbwheel switches 33–35 over lines 125–127 through a 3:8 decoder 130 over line 132 to the microprocessor 120. The rotary switches or thumbwheels 33–35 also provide signals over leads 134–139 (two output signals per switch) to an 8:1 multiplexer (MUX), which, in turn, communicates with the microprocessor 120 over line 140.

The motor 45 is controlled by pulse width modulation, essentially by control of the duty cycle and length of the duty cycle. The control is effected, via the microprocessor, as determined by the parameters associated with the other elements of the circuit. The following is a partial listing of parameters and a partial program listing of the primary functions performed by the circuitry of FIG. 7. The variables associated with the duty cycle of the motor 45 and length of time of actuation of the motor 45 during a pump cycle control the fluid flow parameters, that is, fluid flow rate, desired fluid volume and cycles per day. The variables for motor and pumping control are as follows:

```
                            ; motor speed control parameters
                            ; 1 = 1/20 = 5%, DON/DCNT
                            ; 19 = 19/20 = 95%
                            ; 20 = 20/20 = 100%
        DON: DFB               ; duty on, motor FET on = DON / DCNT
        DCNT: DFB              ; duty count, count DLEN -> 0 over duty cycle
        DLEN: EQU              ; length of duty cycle
        DSTART: EQU            ; default duty for starting motor from dead stop
        DUTRUN: EQU            ; default duty during intake and pump
        MPREC: DFB             ; motor current speed, 4 msec ticks in last rev
        MCURC: DFB             ; motor 4 msec ticks in current revolution
        MTARC: EQU             ; motor target speed, 5*4.096 msec; 20 msec / rev
                            ;
```

-continued

```
STRTIM: DFB         ; 4 msec count down, length of start period, 100 msec
INTTIM: DFB         ; 4 msec count down, length of intake period
PMPTIM: DFB         ; 4 msec count down, length of pump period
CSTTIM: DFB         ; 4 msec count down, length of coast period
                    ;
INTREV: DFB         ; motor rev count during intake period
PMPREV: DFB         ; motor rev count during pump period
CYCTIM0: DFB        ; pump time allowed for 1 complete cycle
CYCTIM1: DFB        ; 3 seconds worth of 4.096 msec ticks = 732
TOTAL0: DFB         ; 4, total pump cycles continuous or intermittent
TOTAL1: DFB         ; 5, starts counting from zero
VOLDEL0: DFB        ; 6, infusion strokes delivered, count to switch value
VOLDEL1: DFB        ; 7, compared to VOLREQ0 & VOLREQ1
VOLREQ0: DFB        ; 8, infusion volume request, 16 bits, 6,553 ml max
VOLREQ1: DFB        ; 9,
TIMSTR:             ;   time keeping variables, clear at infusion start
USEC0: DFB          ;| 10, usec count, 4096 usec per timer tick
USEC1: DFB          ;| 11, 100,000 usec = .1 second = carry into RTCMSEC
USEC2: DFB          ;| 12, 16,777,215 = max count = 16+ seconds
RTCMSEC: DFB        ;| 13, 0–9 Real Time Clock .1 seconds
RTCSEC: DFB         ;| 14, 0–59 Real Time Clock seconds
RTCMIN: DFB         ;| 15, 0–59 RTC clock minutes
RTCHOUR: DFB        ;| 16, 0–255 RTC clock hrs since infuse start
                    future time value, when RTC match, pump
PMPMSEC: DFB        ;| 17, infusion alarm .1 secs, start nexpump cycle
PMPSEC: DFB         ;| 18, infusion alarm seconds
PMPMIN: DFB         ;| 19, infusion alarm minutes
PMPHOUR: DFB        ;| 20, infusion alarm hours
INTMIN: DFB         ;| 21, intermittent alarm minutes
INTHOUR: DFB        ;| 22, intermittent alarm hour
TIMEND:             ;|   label marks end of time variables
        For flow rate and fluid volume, the parameters are as follows:
                    ; rate and volume settings-
                    ; determined by rotary switch settings
                    ;
RATEMS: DFB         ;| 23, infusion rate, .1 sec
RATESEC: DFB        ;| 24, infusion rate, second
RATEMIN: DFB        ;| 25, infusion rate, minute
                    ;|
CYCHR: DFB          ;| 26, hours between intermittent cycles
                    ;|
KFLOSEC: DFB        ;| 27, KVO rate, seconds
KFLOMIN: DFB        ;| 28, KVO rate, minutes
                    ;|
DSTR: DFB           ;| 29, duty during 100 msec start period
DINT: DFB           ;| 30, duty during intake period
DPMP: DFB           ;| 31, duty during pump period
                    ;|
STRREV: DFB         ;| 32, motor rev count during start period
CSTREV: DFB         ;| 33, motor rev count during coasting
                    ;|
                    ;| end of variables output for diagnostics
VAREND:             ;| variable ending address, zpage
```

In the program, certain events generate flag conditions, the variables of which are as follows:

```
            ; FLAGS, bit definitions
FLG1: DFB   00H     ; 8 flag bits in FLG1
            ;
PMPCYC: EQU    0    ; time for an infusion pump cycle, cont. or int.
INTCYC: EQU    1    ; intermittent, time to begin intermittent cycle
TESTF1: EQU    2    ; test input, TP2 diagnostic request
LOBF1: EQU     3    ; low battery flag
BPFLG1: EQU    4    ; beep flag, for running or continuous alarm condition FLG2: DFB           ; 8 flag bits in FLG2

LITEF2: EQU    0    ; previous worm photo transistor reading
MSTRF2: EQU    1    ; motor in start part of pump cycle
MINTF2: EQU    2    ; motor in intake part of pump cycle
MPMPF2: EQU    3    ; motor in pump part of pump cycle
MCSTF2: EQU    4    ; motor in coast part of pump cycle
SWEF2: EQU     5    ; switch error, a rotary switch wiper lost contact
```

-continued

| | | |
|---|---|---|
| SWCF2: EQU | 6 | ; switch contact made, used to find multiple closure |
| FLG3: DFB | | ; 8 flag bits in FLG3 |
| CONRUN: EQU | 0 | ; running, continuous |
| INTRUN: EQU | 1 | ; running, intermittent |
| KVORUN: EQU | 2 | ; running, keep vein open |
| EZDONE: EQU | 3 | ; volume delivered >= volume requested |
| STOPF3: EQU | 4 | ; stop pumping, stall or high pressure detected |
| PRESF3: EQU | 5 | ; records high pressure detection |

The microprocessor 120 has provision for six bit and eight inputs and outputs, the contents of which are defined as follows:

| | | |
|---|---|---|
| | ; define bits in PBDAT | |
| PBOUT: EQU | | ; PB outputs, 3:8 select, motor, IR leds |
| SWSEL0: EQU | 0 | ; lsb of switch selector bits |
| SWSEL1: EQU | 1 | ; |
| SWSEL2: EQU | 2 | ; |
| MTRLED: EQU | 3 | ; motor infrared LED, 1 = light on |
| WGLED: EQU | 4 | ; worm gear infrared LED, 1 = light on |
| MTRFET: EQU | 5 | ; = 1 turns on motor, both pump and fill |
| | ; define bits in PADAT | |
| PAOUT: EQU | | ; PA outputs, 8:1 select, 3:8 enable |
| TPAOUT: EQU | | ; PA outputs, add SERDAT to bits above |
| INSEL0: EQU | 0 | ; out, 8:1 mux select; rot sw, status, slide switch |
| INSEL1: EQU | 1 | ; out, |
| INSEL2: EQU | 2 | ; out, |
| WIPER: EQU | 3 | ; in, mux output, read selected switch line |
| LIGHT: EQU | 3 | ; , same as wiper except photo transistors selected |
| STATUS: EQU | 3 | ; , same as wiper except status line selected |
| EN38: EQU | 4 | ; out, enable 3:8 decode when true |
| SCL: EQU | 4 | ; , serial clock to XICOR chip |
| SERDAT: EQU | 5 | ; in & out, diagnostic i/o for test |
| SDA: EQU | 5 | ; , serial data to XICOR chip |
| GRNLED: EQU | 6 | ; out, green led and speaker |
| REDLED: EQU | 7 | ; out, red led and speaker |
| GLED: EQU | | ; data byte for PADAT |
| RLED: EQU | | ; data byte for PADAT |

The microprocessor is also programmed to determine a number of other parameters. Such as STOP state, on/off switch in OFF position or latch just opened or infusion done or low battery level. For operation, the program routine is as follows:

```
                ; START RUN, enter the run state, either continuous or intermittent
        ;
START:  JSR RDRSW                   ; read the rotary switches
        BRCLR SWEF2,FLG2, START1    ; proceed if switch read error free
        JSR B2RED                   ; 2 beeps for switch error
        BRA SLEEP                   ; go back to sleep on switch error
START1: BRCLR EZDONE,FLG3,START2    ; branch if done flag cleared
        JSR BDONE
        BRA SLEEP                   ; back to sleep after done beeps
START2:
        ;
        ; temporary code to test intermittent alarm
        ;
        BRCLR TESTF1,FLG1,START3    ; bypass if not in test mode
        LDA TOTAL0                  ; least sig byte of pump stroke count
        BOZ START3                  ; bypass if nothing pumped yet
        LDA INTHOUR
        STA RTCHOUR                 ; real time hour = intermittent hour
        LDA INTMIN
        BOZ TEST1
        DECA            ; real time min = intermittent minute − 1
        BRA TEST2
TEST1:  DEC RTCHOUR                 ; real time hour = intermittent hour − 1
        LDA #59D                    ; real time min = 59
TEST2:  STA RTCMIN
        ;
        ; end temporary code to test intermittent alarm
        ;
START3: BCLR STOPF3,FLG3            ; clear stop flag to allow at least 1 stroke
        LDA #05D                    ; 5 seconds
        STA ALRTSEC                 ; time between run blinks of the grn led
        SEI             ; disable interrupts
        JSR BPARM                   ; set BPFLG1 and the next beep time
        BCLR BPFLG1,FLG1            ; no need for an immediate beep
        LDA CYCHR                   ; hours between intermittent cycles
        BOZ START4                  ; branch if hours=0, run continuous
                ;
        BSET KVORUN,FLG3            ; RUN KVO, will immediately go to intermit.
        JSR INTARM                  ; set INTCYC flag and next alarm time
        BRA RUN                     ; begin by waiting
                ;
START4: BSET CONRUN,FLG3               RUN CONTINUOUS, initial flag setup
        JSR PMPARM                  ; set PMPCYC flag and next alarm time
                        ; begin by waiting, will pump next timer
        ; RUN WAIT, resume after timer interrupt, every 4.096 msec
        ;
RUN:    WAIT                        ; leave WAIT every 4.096 msec timer interrupt
                        ; <− timer interrupt serviced here
        CLI                         ; allows next interrupt outside WAIT
        BIL RUN1                    ; proceed if on/off slide switch still ON
        JSR BSW                     ; switch beep for slide switch ON −> OFF
RUN0:   BRA SLEEP                   ; go to sleep if off, ok to resume
                        ; check run flags
RUN1:   BRCLR STOPF3,FLG3,RUN2      ; branch if not stopped by stall or pressure
        BRCLR BPFLG1,FLG1,RUN       ; branch if stopped and not beep time
        BCLR BPFLG1,FLG1            ; time to beep, clear the beep flag
        JSR B4RED                   ; 4 red beeps
        BRA RUN                     ; done
RUN2:   BRCLR BPFLG1,FLG1,RUN3      ; branch if running and not time to blink grn
        BCLR BPFLG1,FLG1            ; clear the alert flag, next blink in 5 sec
        JSR BLINK                   ; 4 msec blink of the green led
        BRCLR TESTF1,FLG1,RUN3      ; skip diagnostic output if no test input
        JSR SOUT                    ; every 5 seconds
                ;
RUN3:   BRSET INTRUN,FLG3,RUN5      ; intermittent run flag set, go to intermit.
        BRSET KVORUN,FLG3,RUN7      ; KVO run flag set, to to KVO run
        BRCLR CONRUN,FLG3,RUN0      ; not cont., intermit., or KVO; go to sleep ; CONTINUOUS RUN
        BRCLR PMPCYC,FLG1,RUN       ; pump alarm not set, return to wait
        BCLR PMPCYC,FLG1            ; clear the flag
        BSR PUMP                    ; do a pump stroke
        JSR VOLCMP                  ; compare delivered and requested
        BRCLR EZDONE,FLG3,RUN       ; continue pumping if not done
RUN4:   JMP IDONE                   ; infusion done, clear flags and quit ; INTERMITTENT RUN
RUN5:   BRCLR PMPCYC,FLG1,RUN       ; pump alarm not set, return to wait
        BCLR PMPCYC,FLG1            ; clear the flag
```

```
       BSR PUMP               ; do a pump stroke
       JSR TOTCMP             ; compare intermittent + KVO and 100 ml
       BRSET EZDONE,FLG3,RUN4     ; cassette empty, clear flags and quit
       JSR VOLCMP             ; compare delivered and requested
       BRCLR EZDONE,FLG3,RUN6     ; continue pump if not done, 2 steps to RUN
                ;
                ; TRANSITION INT RUN -> KVO RUN
       BCLR INTRUN,FLG3       ; this intermittent cycle is done
       BSET KVORUN,FLG3       ; switch from infuse to KVO
       JSR RDRSW              ; next alarm time will be KVO
       SEI                    ; disable interrupts
       JSR PMPARM             ; set PMPARM for the next KVO pump cycle
       BCLR PMPCYC,FLG1       ; don't do a KVO pump stroke until alarm time
RUN6:  JMP RUN
                ;
                ; KVO RUN
RUN7:  BRCLR PMPCYC,FLG1,RUN8     ; pump alarm not set, check cycle alarm
       BCLR PMPCYC,FLG1       ; clear the flag
       BSR PUMP
       JSR TOTCMP             ; compare intermittent + KVO and 100 ml
       BRCLR EZDONE,FLG3,RUN9     ; cassette not empty, keep running
       BRA IDONE              ; cassette empty, infusion done
RUN8:  BRCLR INTCYC,FLG1,RUN9     ; no change from KVO cycle, go wait, 2 steps
                ;
                ; TRANSITION KVO RUN -> INT RUN
       BCLR INTCYC,FLG1       ; clear the alarm flag
       BCLR KVORUN,FLG3       ; suspend the KVO pumping
       BSET INTRUN,FLG3       ; start an intermittent cycle
       CLR VOLDEL0            ; clear infusion volume delivered
       CLR VOLDEL1
       JSR RDRSW              ; restore pump alarm to infuse rate
       SEI                    ; disable interrupts
       JSR PMPARM             ; set PMPCYC and next infusion alarm time
RUN9:  JMP RUN
```

The following routine is directed to the pumping activities.

```
PUMP:
       JSR DLIM               ; limit duty values to legal ranges
       JSR MOTOR              ; run motor 1 pump cycle = 1 worm gear rev
                ;
       BRSET STOPF3,FLG3,PUMP3    ; branch if stall condition detected
       LDA DINT               ; check pressure by comparing duty cycles
       ASLA                   ; accum = 2 * DINT, intake duty
       CMP DPMP               ; C = 1 if 2 * DINT <DPMP
       BCS PUMP2              ; branch if pressure ok
       BRCLR PRESF3,FLG3,PUMP1    ; branch if previous stroke pressure was ok
       BSET STOPF3,FLG3       ; current and previous pressure high, stop
       BRA PUMP3              ; change state from pumping to stop & alert
PUMP1: BSET PRESF3,FLG3       ; flag the first occurrence of high pressure
       BRA PUMP4              ;
PUMP2: BCLR PRESF3,FLG3       ; pressure level ok, clear flag for previous
       BRA PUMP4
PUMP3: LDA #15D               ; alert time interval = 15 seconds
       STA ALRTSEC
       SEI                    ; disable interrupts
       JSR BPARM              ; alarm set for 15 seconds in the future
       BSET BPFLG1,FLG1       ; will cause the error alert in 4 msec
       JMP RUN                ; go wait with stop & alert condition
                ;
PUMP4: INC TOTAL0             ; increment total pump cycle count
       BNZ PUMP5
       INC TOTAL 1            ; carry to total most sig byte
PUMP5: INC VOLDEL0            ; increment infusion volume delivered
       BNZ PUMP6
       INC VOLDEL1
PUMP6: BRCLR TESTF1,FLG1,PUMP7    ; if TESTF1 set, serial output
JSR SOUT                      ; serial output to test equipment
PUMP7: RTS             ;
                ;
                ;
IDONE: JSR BDONE              ; infusion is done, beep once
       BCLR CONRUN,FLG3       ; clear all run flags
       BCLR INTRUN,FLG3
       BCLR KVORUN,FLG3
```

```
    BSET EZDONE,FLG3
    JMP SLEEP
```

The user selectable fluid flow parameters are set out hereafter.

```
    ; DATA
    ;
    ; Infusion Rate data, time between .1 ml pump strokes
    ; data for IRATE, switch 1, is minutes, seconds and .1 seconds
    ;
    ; variable RATEMIN RATESEC RATEMS
    ;
    ; dimension   min    sec    .1sec    SW#    EZFPT5
    ;
RATEDAT:
    DFB         15D,    0D,    0        ; 0      .4 ml/hr
    DFB         7D,    30D,    0        ; 1      .8
    DFB         5D,     0D,    0        ; 2     1.2
    DFB         1D,    12D,    0        ; 3     5
    DFB         0D,    36D,    0        ; 4    10
    DFB         0D,    24D,    0        ; 5    15
    DFB         0D,    18D,    0        ; 6    20
    DFB         0D,    14D,    4        ; 7    25
    DFB         0D,    12D,    0        ; 8    30
    DFB         0D,     9D,    0        ; 9    40
    DFB         0D,     7D,    2        ;10    50
    DFB         0D,     6D,    0        ;11    60
    DFB         0D,     3D,    6        ;12   100
    DFB         0D,     2D,    4        ;13   150
    DFB         0D,     1D,    8        ;14   200
    DFB         0D,     1D,    4        ;15   250
    ;
    ;
    ; Infusion Volume, 16 bits
    ; data for VSW is for 10 pump cycles / ml volume
    ;
    ; variable VOLREQ1 VOLREQ0
    ;
    ; dimension   pump     pump
    ;             cycles   cycles
    ;
    ;             high     low     SW#
    ;             byte     byte
    ;
VOLDAT: DFB      00H     032H     ; 0    5 ml * 10 = 50 = 32H
    DFB          00H,    064H     ; 1   10
    DFB          00H     0C8H     ; 2   20
    DFB          01H     02CH     ; 3   30
    DFB          01H     090H     ; 4   40
    DFB          01H     0F4H     ; 5   50
    DFB          02H     058H     ; 6   60
    DFB          02H     0BCH     ; 7   70
    DFB          03H,    020H     ; 8   80
    DFB          03H,    084H     ; 9   90
    DFB          03H,    0E8H     ;10  100
    DFB          04H     0E2H     ;11  125
    DFB          05H,    0DCH     ;12  150
    DFB          06H,    0D6H     ;13  175
    DFB          07H     0D0H     ;14  200
    DFB          09H     0C4H     ;15  250
    ;
    ;
    ;Intermittent Cycle Rate, number of cycles per day
    ;data for CSW is Hours between cycles
    ;
    ; variable   CYCHR KFLOMIN KFLOSEC
    ;
    ; dimension   hour    min    sec      SW#     cycles    KVO
    ;                            per day
    ;
CYCDAT: DFB              0D,    0D,    0D      0         continuous -
    DFB          24D,   15D,    0D      ;1      1          .4 ml/hr
    DFB          12D,   15D,    0D      ;2      2          .4
    DFB           8D,   15D,    0D      ;3      3          .4
    DFB           6D,   15D,    0D      ;4      4          .4
```

| | | | | | | |
|---|---|---|---|---|---|---|
| DFB | 4D, | 15D, | 0D | ; 5 | 6 | .4 |
| DFB | 24D, | 7D, | 30D | ; 6 | 1 | .8 ml/hr |
| DFB | 12D, | 7D, | 30D | ; 7 | 2 | .8 |
| DFB | 8D, | 7D, | 30D | ; 8 | 3 | .8 |
| DFB | 6D, | 7D, | 30D | ; 9 | 4 | .8 |
| DFB | 4D, | 7D, | 30D | ; 10 | 6 | .8 |
| DFB | 24D, | 5D, | 0D | ; 11 | 1 | 1.2 ml/hr |
| DFB | 12D, | 5D, | 0D | ; 12 | 2 | 1.2 |
| DFB | 8D, | 5D, | 0D | ; 13 | 3 | 1.2 |
| DFB | 6D, | 5D, | 0D | ; 14 | 4 | 1.2 |
| DFB | 4D, | 5D, | 0D | ; 15 | 6 | 1.2 |

For fluid flow calculations, the following applies:

```
VOLCMP:                         ; compare delivered and requested
    BCLR EZDONE,FLG3                ; will set flag if delivered >= requested
    LDA VOLDEL1                 ; most sig, pump stroke count delivered
    CMP VOLREQ1                 ; C = 1 if VOLDEL1 < VOLREQ1
    BCS VOLC2                   ; branch if more pumping required
    BNE VOLC1                   ; branch if done, VOLDEL1 > VOLREQ1
        ; the above branch is unexpected
    LDA VOLDEL0
    CMP VOLREQ0                 ; C = 1 if VOLDEL0 < VOLREQ0
    BCS VOLC2                   ; branch if more pumping required
VOLC1: BSET EZDONE,FLG3             ; flag the done condition
VOLC2:RTS
        ;
TOTCMP:                         ; compare total delivered and 100 ml
    BCLR EZDONE,FLG3                ; will set flag if total >= 100 ml
    LDA TOTAL1                  ; KVO + intermittent = 1000 decimal strokes
    CMP #003H                   ; C = 1 if TOTAL1 < 03
    BCS TOTC1                   ; branch if more intermittent pumping req
    LDA TOTAL0                  ; 1000 decimal = 3E8 hex
    CMP #0E8H                   ; C = 1 if TOTAL0 < E8
    BCS TOTC1                   ; branch if more intermittent pumping req
    BSET EZDONE,FLG3                ; flag the done condition
TOTC1: RTS
                        ;
                        ; MOTOR SPEED CONTROL AND ERROR DETECTION
                        ;
                        ; OBJECTIVE: run motor thru 4 stages -
                        ; START - adjust DSTR so motor rotational speed is
                        ;   approx 20 msec/rev after 100 msec
                        ; INTAKE - run for approx 20 revolutions
                        ;   adjust DINT for 20 msec/rev
                        ; PUMP - run for approx 22 revolutions
                        ;   adjust DPMP for 20 msec/rev
                        ; COAST - count coasting revolutions with
                        ;   motor off, typically 3 rev
                        ;
                        ; 1 rev / 12 msec = 81 rps = 4880 rpm
                        ; 1 rev / 16 msec = 61 rps = 3660 rpm
                        ; 1 rev / 20 msec = 48.8 rps = 2930 rpm
                        ;
MOTOR: SEI              ; no interrupts, time keeping maintained
                        ;
                        ; INIT VARIABLES
                        ;
                        ; state flags
    BSET MSTRF2,FLG2            ; on, START, approx 5 rev
    BCLR MINTF2,FLG2            ; off, INTAKE, approx 20 rev
    BCLR MPMPF2,FLG2            ; off, PUMP, approx 22 rev
    BCLR MCSTF2,FLG2            ; off, COAST, approx 3 rev
                        ;
                        ; maximum cycle time
    LDA #0DCH                   ; time allowed for 1 pump cycle
    STA CYCTIM0                 ; 3 seconds = 732 * 4.096 msec
    LDA #02H                    ; 976 = 02DC hex
    STA CYCTIM1                 ; if CYCTIM -> 0, cycle took too long, error
                        ;
                        ; 4 msec counts
    CLR MCURC                   ; MCURC, current 4 msec count rev in progress
    CLR MPREC                   ; MPREC is the previous MCURC count
    LDA #24D                    ; count to zero for start period
    STA STRTIM                  ; 24 * 4.096 msec = 100 msec start time
    LDA #121D                   ; count to zero for pump period
    STA PMPTIM                  ;121 * 4.096 msec = 500 msec pump time
```

-continued

```
        LDA #73D              ; count to zero for coast period
        STA CSTTIM            ; 73 * 4.096 msec = 300 msec coast time ; revolution counts
        CLR STRREV            ; rev count during start 100 msec
        LDA #28D              ; 50 revs/cycle: 25 intake, 25 pump
        SUB CSTREV            ; accum = 28 - coast rev, ( TDC coast = 3 )
        STA INTREV            ; will subtract starting revolutions later
        CLR CSTREV            ; ready to count coasting revs for this cycle
        LDA #22D              ; worm gear light shines 3 rev before end
        STA PMPREV            ; pump revolutions, allows 3 rev for coasting JSR SDUTY             ; -, 0, start the duty cycle running
        ;                     , 50 machine cycles per step thru
        ;                     , duty cycle, use 19 between JSR's
        ;                     , use 18 between BSR's BRSET MSTRF2,FLG2,MTR11    ; 5, 5, don't look for end while starting
        BRSET MCSTF2,FLG2,MTR11    ; 5, 10, don't look while coasting to stop
        BSET WGLED,PBDAT           ; 5, 15, turn on light for worm gear LED
        JSR DUTY              ; -, 0, duty routine every 19 machine cycles
        BRSET LIGHT,PADAT,MTR10;   ; 5, 5, branch if no light passing ; worm gear at end, start coasting
        CLR DON               ; 4, 9, duty = 0 shuts off motor for coast
        BCLR MINTF2,FLG2      ; 5, 14, transition from either intake
        BCLR MPMPF2,FLG2      ; 5, 19, or pump to coast
        JSR DUTY              ; -, 0, duty routine every 19 machine cycles
        BSET MCSTF2,FLG2      ; 5, 5, set coast state MTR11:  BRSET TOF,TCONT,MTR12      ; 5, 15, timer overflow, 4.096 msec passed MTR12:  LDA #TOIE             ; 2, 17, timer overflow interrupt enable
        JSR DUTY              ; -, 0, duty routine every 19 machine cycles
        STA WCHDOG            ; 4, 4, computer operating properly, COP
        STA TCONT             ; 4, 8, clear timer flag, keep timer running LDA USEC1             ; 3, 12, least usec count * 256
        ADD #16D              ; 2, 14, 16 * 256 = 4096 dec = 1000 hex
        STA USEC1             ; 4, 18, duty sub doesn't affect the carry
        JSR DUTY              ; -, 0, duty routine every 19 machine cycles
        BCC MTR13             ; 3, 3, check carry to next byte
        INC USEC2             ; 5, -, add 65,536 usec MTR13:  DEC CYCTIM0           ; 5, 8, total time allowed for a pump cycle
        BNZ MTR15             ; 3, 11 branch if least sig byte > 0
        DEC CYCTIM1           ; 5, 16, borrow from most sig byte
        BNZ MTR15             ; 3, 19, branch if time is left to finish
MTR14:  INC DSTR              ; -, , increase starting duty
        INC DINT              ; -, , increase intake duty
        INC DPMP              ; -, , increase pump duty
        JMEP MERROR           ; -, , cycle > 4 second -or- rev > 1 second MTR15:  LDA MCURC             ; 3, 14, current motor 4 msec tick count
        INCA                  ; 3, 17, count additional time this rev
        BSR DUTY              ; -, 0, duty routine every 19 machine cycles
        STA MCURC             ; 4, 4,
        CW #244D              ; 2, 6, C = 1 if MCURC < 244
        BCC MTR14             ; 3, 9, branch if this rev too long, > 1 sec MTR16:  BRSET MSTRF2,FLG2,MTR17    ; 5, 14, branch if in start period
        BRSET MINTF2,FLG2,MTR21    ; 5, 19, branch if in intake period
        BSR DUTY              ; -, 0, duty routine every 19 machine cycles
        BRSET MPMPF2,FLG2,MTR22    ; 5, 5, branch if in pump period
                              ; not start, intake, pump: is coast ; , COAST - time countdown
        DEC CSTTIM            ; 3, 8, not start, intake or pump: is coast
        BNZ MTR34             ; 3, 11, branch if coasting time left
        JMP MEXIT             ; 3, 14, one pump cycle complete, exit ; ,START - time countdown
MTR17:  DEC STRTIM            ; 5, 19, count down 100 msec start time
        BSR DUTY              ; -, 0, duty routine every 19 machine cycles
        LDA STRTIM            ; 3, 3, start done when start time = 0
        BNZ MTR32             ; 3, 6, branch if still in start period BCLR MSTRF2,FLG2      ; 5, 11, transition: START -> INTAKE
        BSET MINTF2,FLG2      ; 5, 16, begin intake period
```

-continued

```
        LDA DINT                ; 3, 19, switch duty from start to intake
        BSR DUTY                ; -, 0, duty routine every 19 machine cycles
        STA DON                 ; 4, 4,
        LDA INTREV              ; 3, 7, intake rev = 28 - coast
        SUB STRREV              ; 3, 10, intake rev = 28 - coast - start
        BPL MTR18               ; 3, 13, avoid a negative value for INTREV
        CLRA                    ; 3, -, default to zero for negative values
MTR18:  STA INTREV              ; 4, 17, rev countdown to BDC
        BSR DUTY                ; -, 0, duty routine every 19 machine cycles
        ASLA                    ; 3, 3, * 2
        ASLA                    ; 3, 6, * 4
        ADD INTREV              ; 3, 9, * 4 + 1 = 5, 4 msec counts per rev
        STA INTTIM              ; 4, 13, time countdown to check run speed
        LDA STRREV              ; 3, 16, motor rev count during start
        CMP #03                 ; 2, 18, C = 1 if STRREV < 3
        BSR DUTY                ; -, 0, duty routine every 19 machine cycles
        BCS MTR19               ; 3, 3, 0,1,2 revs, DSTR+1
        LDA MPREC               ; 3, 6, time for last rev while starting
        CMP #05                 ; 2, 8, C= 1 if MPREC < 5
        BEQ MTR34               ; 3, 11, if equal no change
        BCS MTR20               ; 3, 14, branch if MPREC < 5
        BRN MTR19               ; 3, 17, kill time
        BSR DUTY                ; -, 0, duty routine every 19 machine cycles
        BRN MTR19               ; 3, 3, kill time
MTR19:  INC DSTR                ; 5, 8, MPREC > 5, slow, increase duty
        BRA MTR34               ; 3, 11, proceed to revolution counting
MTR:    DEC DSTR                ; 5, 19, MPREC < 5, fast, reduce duty
        BSR DUTY                ; -, 0, duty routine every 19 machine cycles
        BRA MTR31               ; 3, 3, proceed to revolution counting
        ;
        ;   INTAKE - time countdown
MTR21:  BSR DUTY                ; -, 0, duty routine every 19 machine cycles
        LDA INTTIM              ; 3, 3, decrement time during run, stop at 0
        BOZ MTR32               ; 3, 6, branch if time = 0, slow on intake
        DEC INTTIM              ; 5, 11, if zero at end run then speed slow
        BRA MTR35               ; 3, 14, proceed to revolution counting
        ;
        ;   ,PUMP - time countdown
MTR22:  LDA PMPTIM              ; 3, 8, decrement time during run, stop at 0
        BOZ MTR34               ; 3, 11, branch if time = 0, slow on pump
        DEC PMPTIM              ; 5, 15, if zero at end run then speed slow
        BRA MTR36               ; 3, 18, proceed to revolution counting
        ;
        ;
        ; duty cycle subroutine
        ; use SDUTY for first time
DUTY:   DEC DCNT                ; 5, 5, count down the cycle count
        BOZ SDUTY               ; 3, 8, DCNT = 0, end cycle, reload counts
        DECX                    ; 3, 11, count down the motor on time
        BNZ DUTY1               ; 3, 14, while on count > 0, keep motor on
        BCLR MTRFET,PBDAT       ; 5, 19, FET is off, motor current = 0
DUTY1:  RTS                     ; 6, 25, 25 machine cycles
        ;                       ; start the duty cycle
SDUTY:  LDX #DLEN               ; 3, 3, length of the duty cycle
        STX DCNT                ; 4, 7, duty count variable
        LDX DON                 ; 3, 10, on duty time in the X register
        BOZ SDUTY1              ; 3, 13, if duty = 0, don't turn on motor
        BSET MTRFET,PBDAT       ; 5, 18, turn on the motor current
SDUTY1: RTS                     ; 6, 24
        ;
        ;   , MOTOR REVOLUTION COUNTING
        ;
MTR36:  BSR DUTY                ; -, 0, duty routine every 19 machine cycles ;   LIGHT = 0 - path open
        ;   LIGHT = 1 - path closed
        ;   LITEF2 = previous LIGHT
        ;
        BSET MTRLED,PBDAT       ; 5, 5, turn on LED to check motor rotation
        BRSET LIGHT,PADAT,MTR40 ; 5, 10, branch if light = 1
        ;   ,LIGHT = 0, LITEF2 = ?
        BRCLR LITEF2,FLG2,MTR41 ; 5, 15, branch if LIGHT = LITEF2 = 0
        ;   ,LIGHT = 0, LITEF2 = 1
        BCLR LITEF2,FLG2        ; 5, 20, LIGHT = 0, LITEF2 = 0
        BSRDUTY                 ; -, 0, duty routine every 19 machine cycles
        BRA MTR42               ; 3, 3, a motor revolution detected MTR40:  BSET LITEF2,FLG2        ; 5, 15, LIGHT = 1, LITEF2 = 1, armed
MTR41:  BCLR MTRLED,PBDAT       ; 5,20,
        BSR DUTY                ; -, 0, duty routine every 19 machine cycles
```

```
                JMP MTR1                ; 3, 3, no motor revolution, back to time ;   LIGHT = 0, LITEF2 = 1
                                        ;   LIGHT 1 -> 0, 1 motor revolution
                                        ;
MTR42:  BCLR MTRLED,PBDAT               ; 5, 8, turn off LED as soon as possible
                                        ;   restart the revolution timer
                LDA MCURC               ; 3, 11, current count of 4 msec ticks
                STA MPREC               ; 4, 15, saved current speed count
                CLR MCURC               ; 4, 19, start a new count up
                BSR DUTY                ; -, 0, duty routine every 19 machine cycles ;   ,STATE selection
                BRSET MSTRF2,FLG2,MTR43 ; 5, 5, branch if in start period
                BRSET MINTF2,FLG2,MTR44 ; 5, 10, branch if in intake period
                BRSET MPMPF2,FLG2,MTR48 ; 5, 15, branch if in pump period
                                        ;   ,not start, intake, pump: is coast ;   ,COAST - motor revolution count
                INC CSTREV              ; 5, 20, increment coast rev counter
                BSRDUTY                 ; -, 0, duty routine every 19 machine cycles
                JMP MTR1                ; 3, 3, back to time keeping ;   ,START - motor revolution count
MTR43:  INC STRREV                      ; 5, 10, count up revs during start
        JMP MTR4                        ; 3, 13, back to time keeping ;   ,INTAKE - motor revolution count
MTR44:  DEC INTREV                      ; 5, 15, count down revs in intake period
                BOZ MTR45               ; 3, 18, branch if = 0, end of intake period
                BSR DUTY                ; -, 0, duty routine every 19 machine cycles
                JMP MTR1                ; 3, 3, back to time keeping ; transition INTAKE -> PUMP
MTR45:  BSR DUTY                        ; -, 0, duty routine every 19 machine cycles
                BCLR MINTF2,FLG2        ; 5, 5, quit intake
                BSET MPMPF2,FLG2        ; 5, 10, enter pump period LDA DPMP                ; 3, 13,
                STA DON                 ; 4, 17, switch to pump duty cycle
                BSRDUTY                 ; -, 0, duty routine every 19 machine cycles
                LDA INTTIM              ; 3, 3, adjust DINT
                BNZ MTR46               ; 3, 6, branch if intake time > 0
                INC DINT                ; 5, 11, int time = 0, slow, DINT = DINT + 1
                JMP MTR5                ; 3, 14, back to time keeping
MTR46:  CMP #08D                        ; 2, 8, C = 1 if INTTIM < 8
                BCC MTR47               ; 3, 11, branch if INTTIM > 7, fast
                JMP MTR5                ; 3, 14, int time = 1-7, no speed change
MTR47:  DEC DINT                        ; 5, 16, int time > 7, fast, DINT = DINT - 1
                JMP MTR6                ; 3, 19, back to time keeping ;   ,PUMP - motor revolution count
MTR48:  DEC PMPREV                      ; 5, 20, count down revs in pump period
                JSR DUTY                ; -, 0, duty routine every 19 machine cycles
                LDA PMPREV              ; 3, 3, if pump rev = 0 go to coast
                BOZ MTR49               ; 3, 6, branch if = 0, end of pump period
                JMP MTR3                ; 3, 9, back to time keeping ; transition PUMP -> COAST
MTR49:  BCLR MPMPF2,FLG2                ; 5, 11, quit pump
                BSET MCSTF2,FLG2        ; 5, 16, enter coast period CLR DON                 ; 4, 20, duty = 0 shuts down motor
                JSR DUTY                ; -, 0, duty routine every 19 machine cycles
                LDA PMPTIM              ; 3, 3, adjust DPMP
                BNZ MTR50               ; 3, 6, branch if intake time > 0
                INC DPMP                ; 5, 11, int time = 0, slow, DPMP = DPMP + 1
                JMP MTR5                ; 3, 14, back to time keeping
MTR50:  CMP #08D                        ; 2, 8, C = 1 if PMPTIM < 8
                BCC MTR51               ; 3, 11, branch if PMPTIM > 7, fast
                JMP MTR5                ; 3, 14, pump time = 1-7, no speed change
MTR51:  DEC DPMP                        ; 5, 16, pump time > 7, fast, DPMP = DPMP - 1
                JMP MTR6                ; 3, 19, back to time keeping MERROR: BSET STOPF3,FLG3                ; pump cycle or motor rev too long, stall MEXIT:  BCLR MTRFET,PBDAT               ; motor off, exit may occur any time
```

| | |
|---|---|
| BCLR MTRLED,PBDAT | ; motor led off, same reason as above |
| BCLR WGLED,PBDAT | ; worm gear led off |
| CLR DON | ; exit with duty = 0 |
| CLR PADAT | ; mx select lines can be used for scope time |

The above programs is self-explanatory. In accordance with the foregoing subroutines and program, settings of the thumbwheel switches 33–35 provide the initial inputs of desired flow rate, desired fluid volume and number of cycles of solution flow during a given time period. The microprocessor 120 is provided with an internal clock by which variables are monitored and controlled. The volume of fluid discharged is monitored by the microprocessor 120 in accordance with motor 45 revolutions which are translated into strokes of the pump or piston 58, with each motor revolution being detected by photocell assembly 98 and each cycle of the piston 58 being detected by the photocell 100. During this operation, the time it takes for a push stroke of the piston 58 and the time it takes for a pull stroke of the piston is constantly monitored on a regular periodic basis. Since the time it takes for a push stroke is the time of opening of the discharge valve 88 and the time it takes for a pull stroke is the time of opening of the inlet valve 86, these times, in turn, can be correlated to fluid rate delivery, with the number of actuations of the piston 58 correlating to fluid volume. By constantly keeping track of each cycle and measuring the ratio of the time to open the discharge valve 88 to the time to open the inlet valve 86, and comparing each ratio to the preceding ratio, proper flow can be monitored and controlled, and events such as occlusion can be determined should the ratio change significantly over 3 or more cycles. In the event of an occlusion, the time for moving the piston 58 through a push stroke will increase due to the increase in back pressure as a result of the occlusion. On the other hand, in the event the bag 62 is empty, the time required for moving the piston 58 during a push stroke will decrease due to the lower pressure as a result of the absence of solution. In either event, the above program enables this monitoring and flow control and issues an alarm in the event of significant ratio change over a period of three cycles of the piston 58, and issues an alarm on emptying of the solution bag 62. Thus, by the utilization of the piston 58 interoperatively coupled and actuated by the motor 45 and gears 47, 48, and by means of the program in the motor operation and pump operation routines, the piston and motor gear drive forces are monitored continually during operation of the apparatus 20, with the thus monitored forces or pressures allowing the detection of the occlusion of the IV tubing set 25, or the condition when the bag 62 is empty. These alarm conditions are thus effected via the program without the need for other devices, thus simplifying the apparatus 20.

In accordance with the present invention, the control module 22 and the cassette 24 of the apparatus 20 provides a compact, economical lightweight transportable infusion apparatus which is uncomplicated to set for desired solution flow parameters, and reliable in performance of the intended functions. The cassette is low cost and disposable to facilitate replacement and use. While there has been shown and described a preferred embodiment, it is to be understood that various other adaptations and modifications may be made within the spirit and scope of the invention.

What is claimed is:

1. Infusion apparatus comprising:

a control module having motor means;

a cassette adapted for connection to said control module and having solution containing means therein, said cassette having a side thereof configured for matingly slidably engaging a side of said control module for connecting the two parts together as a unit;

a valve assembly within said cassette for controlling flow of solution from said solution containing means;

a piston member within said valve assembly, said piston member having a head protruding from said side of said cassette; and reciprocable means within said control module protruding from said side thereof and reciprocated by said motor means, said reciprocable means and said head having coacting engaging configurations for enabling releasable attachment with said cassette positioned with its side in abutting relation with said side of said control module with said sides out of alignment, the sliding of one of said cassette and said module relative to the other both interlocking the two parts and engaging said head with said reciprocable means.

2. The apparatus of claim 1 wherein said control module includes a plurality of controls for setting solution discharge parameters and wherein said controls are positioned on said side of said control module for rendering the controls inaccessible with said cassette matingly engaging said control module.

3. The apparatus of claim 2 wherein said controls are thumbwheel switches which protrude slightly through slots in said side of said control module.

4. The apparatus of claim 1 wherein said control module includes microprocessor means electrically coupled to said motor for controlling the operation of the motor.

5. The apparatus of claim 4 wherein said reciprocable means is a piston actuator and said microprocessor means includes means for determining the time duration of the push stroke of said actuator and the pull stroke of said actuator and means for utilizing said time durations for determining operation of said apparatus.

6. The apparatus of claim 5 wherein said microprocessor means includes means for regularly periodically calculating the ratio between said time durations and for emitting an alarm in response to significant changes in the thus-calculated ratio over a number of successive calculated ratios.

7. The apparatus of claim 6 wherein said alarm is an occlusion alarm emitted in response to a significant increase in the time duration of the push stroke of said actuator relative to the time duration of the pull stroke of said actuator.

8. The apparatus of claim 4 wherein said reciprocable means is a piston actuator and wherein said microprocessor means includes means for monitoring actuation of said piston in both directions and determining values related to time of actuation in each direction.

9. The apparatus of claim 8 wherein the determined values relate to the time duration of actuation of said piston in each direction for providing an indication of the force acting against said piston by the solution and said microprocessor means issues an alarm in response to a significant change in values determined by said monitoring means.

10. The apparatus of claim 9 wherein said alarm is one of an occlusion alarm and an empty alarm.

11. The apparatus of claim 1 further including a tubing set connected in fluid flow relation with said valve assembly and wherein said head of said piston member protrudes a distance sufficient to enable manual grasping thereof with said control module separated from said cassette for enabling manual priming of said tubing set.

12. Fluid flow control apparatus comprising:

pump means having a reciprocable piston member in fluid flow communication with the fluid;

motor means;

means interconnecting said motor means and said piston member for reciprocating the same;

means in circuit relation with said motor means for setting desired fluid flow parameters;

means for determining the time duration of movement of said piston member in each direction of travel during operation of said motor means when pumping fluid; and means responsive to the time durations thus determined for determining at least one state of said fluid flow parameters and for controlling said motor means in accordance with said desired fluid flow parameters.

13. The apparatus of claim 12 wherein said control means includes a microprocessor.

14. The apparatus of claim 12 wherein said fluid flow apparatus is an infusion apparatus and further includes tubing for transferring solution to a patient by means of said tubing and wherein said at least one state of fluid flow is an occlusion of fluid flow through said tubing.

15. The apparatus of claim 12 wherein said apparatus includes a control module and a separable cassette and wherein said motor means is contained in said control module and said reciprocable piston is contained in said cassette.

16. The apparatus of claim 15 wherein said cassette includes solution containing means and wherein said pump means includes a chamber in flow communication with first and second valve means within said cassette, said first valve means enabling flow of solution from said solution containing means into said chamber and said second valve means enabling flow of solution from said chamber to an intravenous tubing set.

17. The apparatus of claim 12 wherein said fluid flow apparatus is an infusion apparatus and further includes a solution bag and tubing for transferring solution to a patient from said solution bag by means of said tubing and wherein said at least one state of fluid flow is absence of solution in said bag.

18. The apparatus of claim 12 wherein said infusion apparatus includes a control module having a side with manually operable controls; and a cassette having said piston member and a solution containing means therein with a side of said cassette configured for mating slidable engagement with said side of said control module for connecting the two parts together as a unit, the parts when thus connected together rendering said controls inaccessible, and wherein said interconnecting means is within said control module and includes a portion protruding from said control module side for engagement with and actuation of said reciprocable piston member.

19. The apparatus of claim 18 wherein said portion and said piston have coacting engaging configurations for enabling releasable attachment with said cassette positioned with its side in abutting relation with said side of said control module with said sides out of alignment, the sliding of one of said cassette and said module relative to the other both interlocking the two parts and engaging said portion with said reciprocable piston member.

20. Infusion apparatus comprising:

a control module having manually operable controls for setting solution discharge parameters, said module having a side with said manually operable controls on said side;

a separable cassette having solution containing means therein and a side thereof configured for mating engagement with said side of said control module for connecting the two parts together as a unit, the parts when thus connected together rendering said control means inaccessible; and pumping means, part of which is contained in said control module and part of which is contained in said cassette, said pumping means enabling discharge of solution from said solution containing means in accordance with the setting of said controls, said part of said pumping means within said cassette including a chamber in flow communication with first and second valve means within said cassette, said first valve means enabling flow of solution from said solution containing means into said chamber and said second valve means enabling flow of solution from said chamber to an intravenous tubing set.

21. The apparatus of claim 20 wherein said pumping means includes a reciprocable piston within said chamber and said first valve means is actuable to an open condition on withdraw of said piston and said second valve means is normally closed during the drawing motion of the piston and opens in response to reverse movement of said piston.

22. The apparatus of claim 21 wherein said first and second valve means are each formed as one piece nipple-shaped valve members of elastic material of different durometers to thereby require a different force for actuation of each of said valve means.

23. The apparatus of claim 22 wherein said first valve member is formed of a lower durometer material than said second valve member.

24. The apparatus of claim 23 wherein said first valve member, at the outer end, has a deep single slit with low durometer material to provide minimal resistance, and said second valve member, at the outer end, has a shallow slit and is formed of a higher durometer material to eliminate possible seepage.

25. The apparatus of claim 22 wherein said part of said pumping means within said control module includes means for reciprocating said piston.

26. The apparatus of claim 25 wherein said means for reciprocating said piston includes reciprocable means within said control module protruding from said side thereof and motor means for actuation of said reciprocable means.

27. The apparatus if claim 21 further including microprocessor means for actuating said pumping means, said microprocessor means including means for monitoring actuation of said piston in both directions and determining values related to time of actuation in each direction.

28. The apparatus of claim 27 wherein said microprocessor means issues an alarm in response to a significant change in values determined by said monitoring means.

29. The apparatus of claim 28 wherein said alarm is one of an occlusion alarm and an empty alarm.

30. Fluid flow control apparatus comprising:

a control module;

a separable cassette including solution containing means;

pump means having a reciprocable piston member in fluid flow communication with the fluid, said reciprocable piston being contained in said cassette, and wherein said pump means includes a chamber in flow communication with first and second valve means within said cassette, said first valve means enabling flow of solution from said solution containing means into said chamber and said second valve means enabling flow of solution from said chamber to an intravenous tubing set, and wherein said reciprocable piston is within said chamber and said first valve means is actuable to an open condition on withdraw of said piston and said second valve means is normally closed during the drawing motion of the piston and opens in response to reverse movement of said piston;

motor means contained in said control module;

means interconnecting said motor means and said piston member for reciprocating the same;

means in circuit relation with said motor means for setting desired fluid flow parameters;

means for determining the time duration of movement of said piston member in each direction of travel during operation of said motor means when pumping fluid; and means responsive to the time durations thus determined for determining at least one state of fluid flow and for controlling said motor means in accordance with said desired fluid flow parameters.

31. The apparatus of claim 30 wherein said first and second valve means are each formed as one piece nipple-shaped valve members of elastic material of different durometers.

32. The apparatus of claim 31 wherein said first valve member is formed of a lower durometer material than said second valve member.

33. The apparatus of claim 32 wherein said first valve member, at the outer end, has a deep single slit with low durometer material to provide minimal resistance, and said second valve member, at the outer end, has a shallow slit and is formed of a higher durometer material to eliminate possible seepage.

* * * * *